(12) United States Patent
Brewer et al.

(10) Patent No.: US 7,184,141 B2
(45) Date of Patent: Feb. 27, 2007

(54) OPTICAL FLOW CELL FOR TRIBOLOGICAL SYSTEMS

(75) Inventors: John F Brewer, Mogadore, OH (US); Joseph P Kolp, North Canton, OH (US); David W Miller, Stow, OH (US); Paul C Schweigert, Akron, OH (US); Thomas J Sebok, Tallmadge, OH (US)

(73) Assignee: Lockheed Martin Corporation, Akron, OH (US)

( * ) Notice: Subject to any disclaimer, the term of this patent is extended or adjusted under 35 U.S.C. 154(b) by 377 days.

(21) Appl. No.: 10/806,874

(22) Filed: Mar. 23, 2004

(65) Prior Publication Data

US 2005/0213088 A1    Sep. 29, 2005

(51) Int. Cl.
G01N 1/10 (2006.01)
G01N 21/00 (2006.01)
(52) U.S. Cl. ........................ 356/246; 356/440
(58) Field of Classification Search ............. 356/246
See application file for complete search history.

(56) References Cited

U.S. PATENT DOCUMENTS

| | | | |
|---|---|---|---|
| 3,198,064 A | 8/1965 | Moore | 88/14 |
| 3,947,121 A | 3/1976 | Cotter et al. | 356/38 |
| 4,393,466 A | 7/1983 | Deindoerfer et al. | 364/415 |
| 4,804,267 A | 2/1989 | Greenfield | 356/335 |
| 4,807,267 A | 2/1989 | Rifu et al. | 378/7 |
| 5,030,421 A | 7/1991 | Muller | 422/102 |
| 5,098,661 A | 3/1992 | Froehlich et al. | 422/102 |
| 5,241,189 A | 8/1993 | Vandagriff et al. | 250/575 |
| 5,594,544 A | 1/1997 | Horiuchi et al. | 356/73 |
| 5,766,957 A | 6/1998 | Robinson et al. | 436/165 |
| 5,883,721 A | 3/1999 | Gilby et al. | 356/440 |
| 6,104,483 A | 8/2000 | Sebok et al. | 356/244 |
| 6,290,912 B1 | 9/2001 | Doms | 422/82.05 |
| 6,771,366 B2 * | 8/2004 | Canty et al. | 356/246 |
| 2003/0030810 A1 | 2/2003 | Sebok et al. | 356/436 |

FOREIGN PATENT DOCUMENTS

| | | |
|---|---|---|
| JP | 62-112034 | 5/1987 |
| JP | 7-218417 | 8/1995 |
| WO | WO 95/12118 | 5/1995 |

* cited by examiner

Primary Examiner—Gregory J. Toatley, Jr.
Assistant Examiner—Amanda Merlino
(74) Attorney, Agent, or Firm—Renner Kenner Greive Bobak Taylor & Weber

(57) ABSTRACT

An optical flow is disclosed having a shell with a first portion and a second portion. The first portion provides a light entry aperture, and the second portion provides an imaging aperture. An inlet tube and an outlet tube are retained between the first portion and the second portion. A viewing assembly is retained between the first portion and the second portion. The viewing assembly includes a reference plate and a flow channel. The flow channel fluidly communicates with the inlet tube and the outlet tube. The reference plate extends from the shell to serve as a repeatable reference point for properly positioning the optical flow cell.

14 Claims, 6 Drawing Sheets

OPTICAL FLOW CELL FOR TRIBOLOGICAL SYSTEMS

TECHNICAL FIELD

The present invention relates generally to fluid inspection systems. More particularly, the invention relates to an optical flow cell through which the fluid under inspection passes. Specifically, the invention relates an optical flow cell which provides an accurate reference point for repeatable analysis of the fluid by an imaging system contained in the fluid inspection system.

BACKGROUND ART

It is known to provide fluid sampling devices using optical near-field imaging. Such a device is employed to determine quantity, size, physical characteristics, and types of particulate matter in fluids. Examples of fluids which are monitored in such a system are lubricating oils used in engines and rotating machinery; hydraulic fluids used in equipment; and fluids used in industrial quality control, food processing, medical analysis, and environment control. In its most common use, such a device monitors engine oil for particulate debris, wherein a quantity, size, and shape of particulates correspond to an engine condition, and can alert one to particular problems with the engine. Predicting failure is critically important in aircraft engines to avoid accidents and loss of life.

The early stages of engine wear cause small particulate matter, of about 50 microns or less in size, to be generated. These particulates have characteristic shapes indicative of the type of wear produced by specific wear mechanisms. As the wear process progresses, the quantity and size of particulates increase. Accordingly, sensing and identifying smaller particles allows early identification of faults, thus, allowing more time for corrective maintenance and preventing unexpected catastrophic failures.

Although current devices such as the optical flow cell disclosed in U.S. Pat. No. 6,104,483, which is incorporated herein by reference, are sufficient in their stated purpose, such devices can be difficult to mass produce because they are manufactured using a potting process. For example, during the potting process, a viewing assembly along with an inlet tube and an outlet tube are positioned in a mold, and the mold is thereafter filled with a bonding material (i.e. epoxy resin).

The bonding material ultimately cures around the inlet tube, outlet tube, and viewing assembly to form the body of the optical flow cell. However, placement of the above-discussed components in the mold, and providing access to the viewing assembly is difficult. For example, the positioning of the inlet tube, outlet tube, and viewing assembly must be precisely accomplished. Therefore, considerable time is spent arranging the components in the mold, and insuring that the components are aligned as the bonding material fills the mold. Furthermore, to insure access through the body to the viewing assembly, various plungers or other inserts must be used to form a light entry aperture and an imaging aperture. The plungers or other inserts are positioned on either side of the viewing assembly prior to filling the mold with bonding material. The placement of the plungers or other inserts further complicates placement of the components in the mold, and the overall manufacture of the optical flow cell.

After the bonding material cures, a "potted" part is removed from the mold, and the plungers or other inserts, as well as extraneous epoxy resin are trimmed from the part. Thereafter, the part is cleaned, and additional epoxy is applied around the periphery of the light entry aperture to form a finished optical flow cell.

As can be appreciated, manufacture of such an optical flow cell is a time-consuming process. Moreover, precise positioning of the above-discussed components in the mold is difficult, thereby requiring additional skilled labor for assembly.

Therefore, there is a need for an optical flow cell which is relatively simple to manufacture. Such an optical flow cell should eliminate the need to use a potting process during manufacture, and be composed of pre-formed structural components. Such components should allow for manufacture of such an optical flow cell within small tolerances, and thereby provide for repeatable reference points.

DISCLOSURE OF THE INVENTION

In general, the present invention contemplates an optical flow cell having a shell with a first portion and a second portion, wherein the first portion provides a light entry aperture, and the second portion provides an imaging aperture, an inlet tube and an outlet tube retained between the first portion and the second portion, and a viewing assembly retained between the first portion and the second portion, wherein the viewing assembly includes a reference plate and a flow channel, the flow channel fluidly communicating with the inlet tube and the outlet tube, and the reference plate extending from the shell to serve as a repeatable reference point for properly positioning the optical flow cell.

BEST MODE FOR CARRYING OUT THE INVENTION

Figure 1:
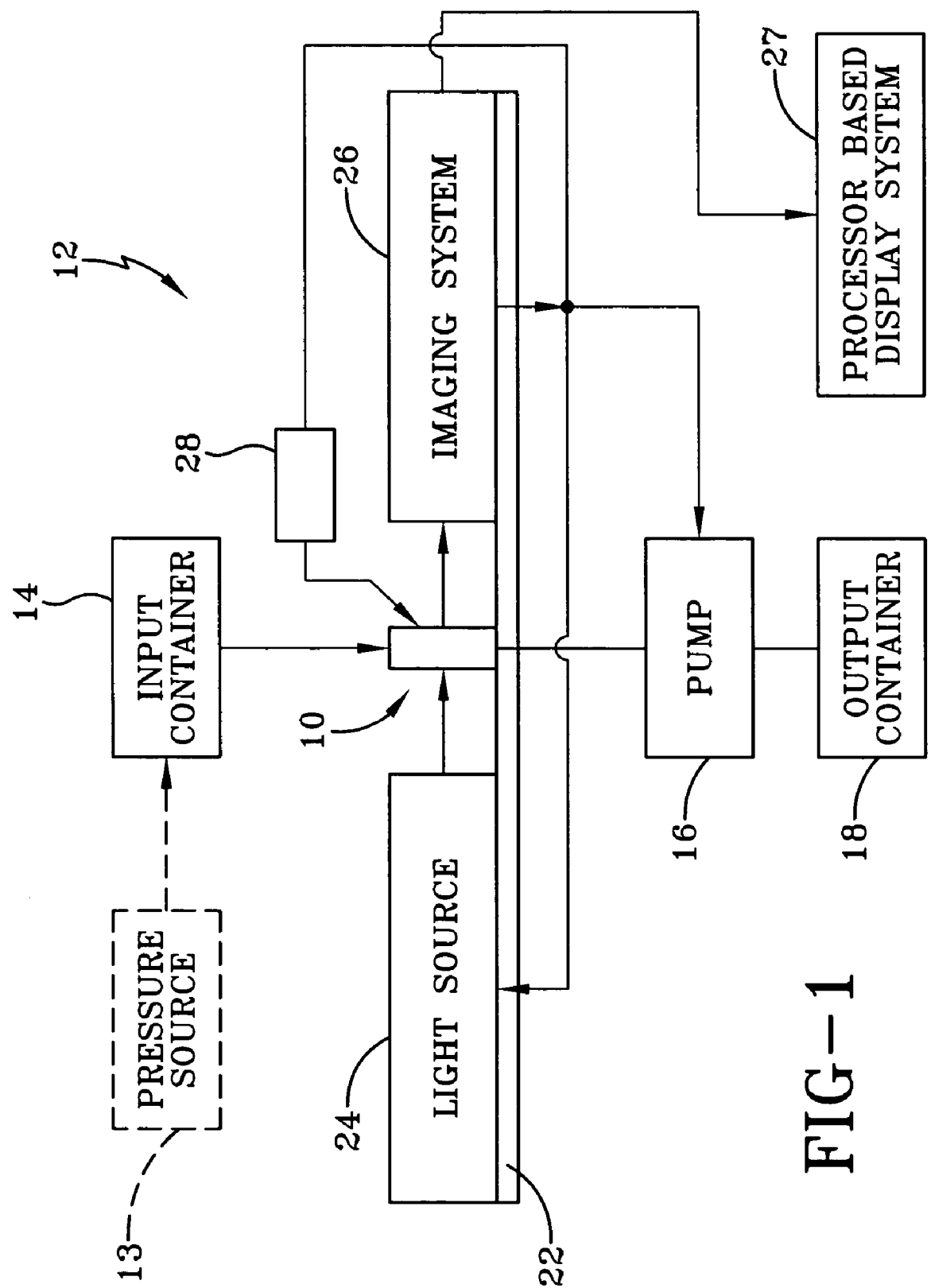
FIG. 1 is a schematic diagram of a flow cell a fluid inspection system which employs an optical flow cell made in accordance with the concepts of the present invention.
Figure 1A:
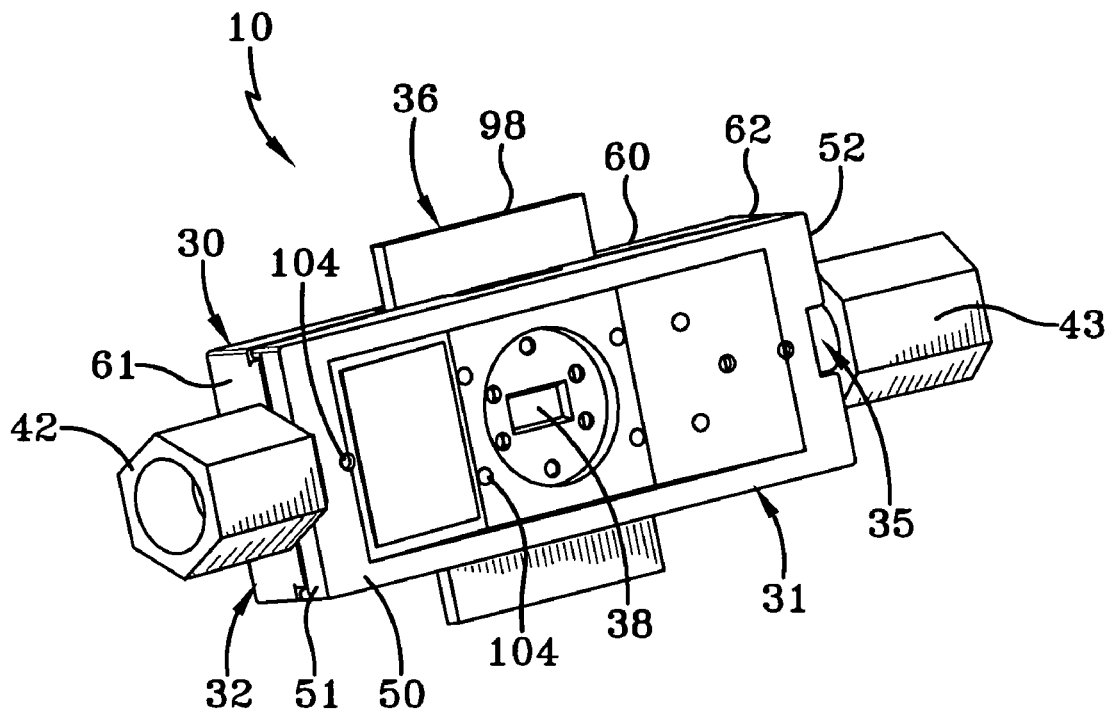
FIG. 1A is a top perspective view of the optical flow cell of FIG. 1.
Figure 1B:
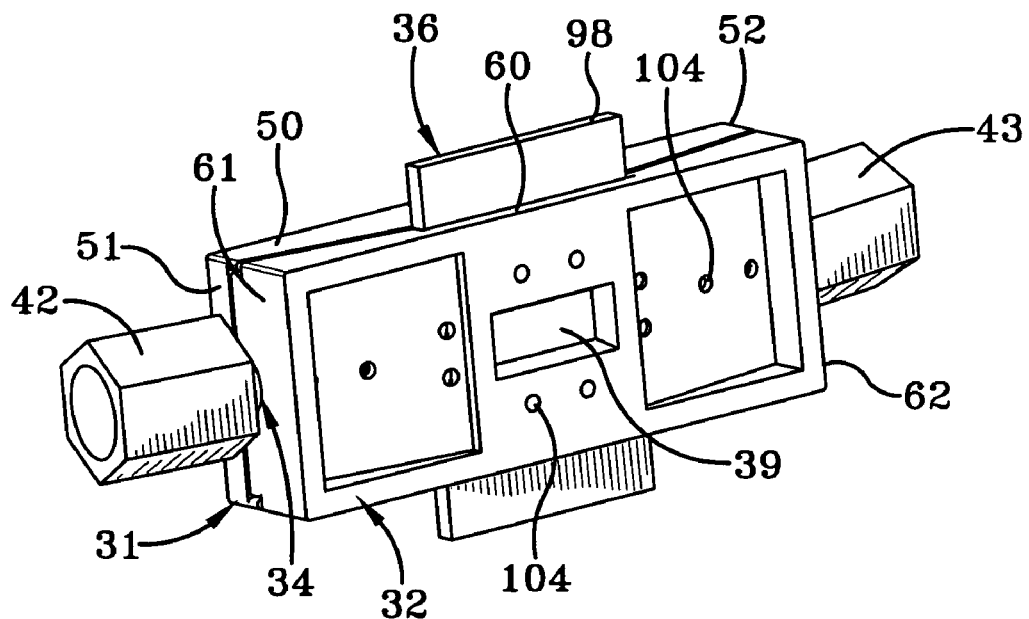
FIG. 1B is a bottom perspective view of the optical flow cell of FIG. 1.

Referring to the drawings, and more particularly to FIGS. 1, 1A and 1B, the optical flow cell of the present invention is designated generally by the numeral 10. The optical flow cell 10 is provided within a fluid sample inspection system 12 as seen in FIG. 1 to aid the analysis of a sample fluid material (not shown). A brief discussion of the fluid sample inspection system 12 will be provided, and then followed by a detailed discussion of the optical flow cell 10.

A pressure source 13 may be coupled to an input container 14 of the sample fluid material. Normally, the input container 14 contains oils that are used to lubricate machine parts, such as engines and transmissions, or other fluid which contains particles that need to be evaluated.

Application of pressure generated by the pressure source 13 to the input container 14 causes the sample fluid material to flow to an input, and through the optical flow cell 10 for analysis. Coupled to an output of the optical flow cell 10 may be a pump 16, which is used to draw the sample fluid material through the optical flow cell 10. Those skilled in the art will appreciate that the pressure source 13 and the pump 16 may be employed in conjunction with one another, or may be operated separately to pass the sample fluid material through the optical flow cell 10. After passing through the optical flow cell 10, the sample fluid material is deposited into an output container 18 for storage, or other purposes.

In the fluid sample inspection system 12, a plate 22 supports the optical flow cell 10. Also supported by the plate 22 is a light source 24, which in the preferred embodiment, employs a laser diode with associated collimating optics to direct light through a viewing assembly of the optical flow cell 10 and into the sample fluid material. The light generated by the light source 24 impinges on the sample fluid material, and generates an image (or shadow) which can be detected by an imaging system 26 that is also supported by the plate 22. The imaging system 26 is coupled to a processor-based display system 27 for classifying the particles, for determining the number of particles contained within the sample, and for analyzing other features of the fluid.

An alternative light source 28, which may be used in conjunction with, or in alternative to the light source 24, may be positioned on an opposite side of the optical flow cell 16. The light source 28 may project a white light to facilitate the detection of the particle's color for further classification or analysis.

Figure 1C:
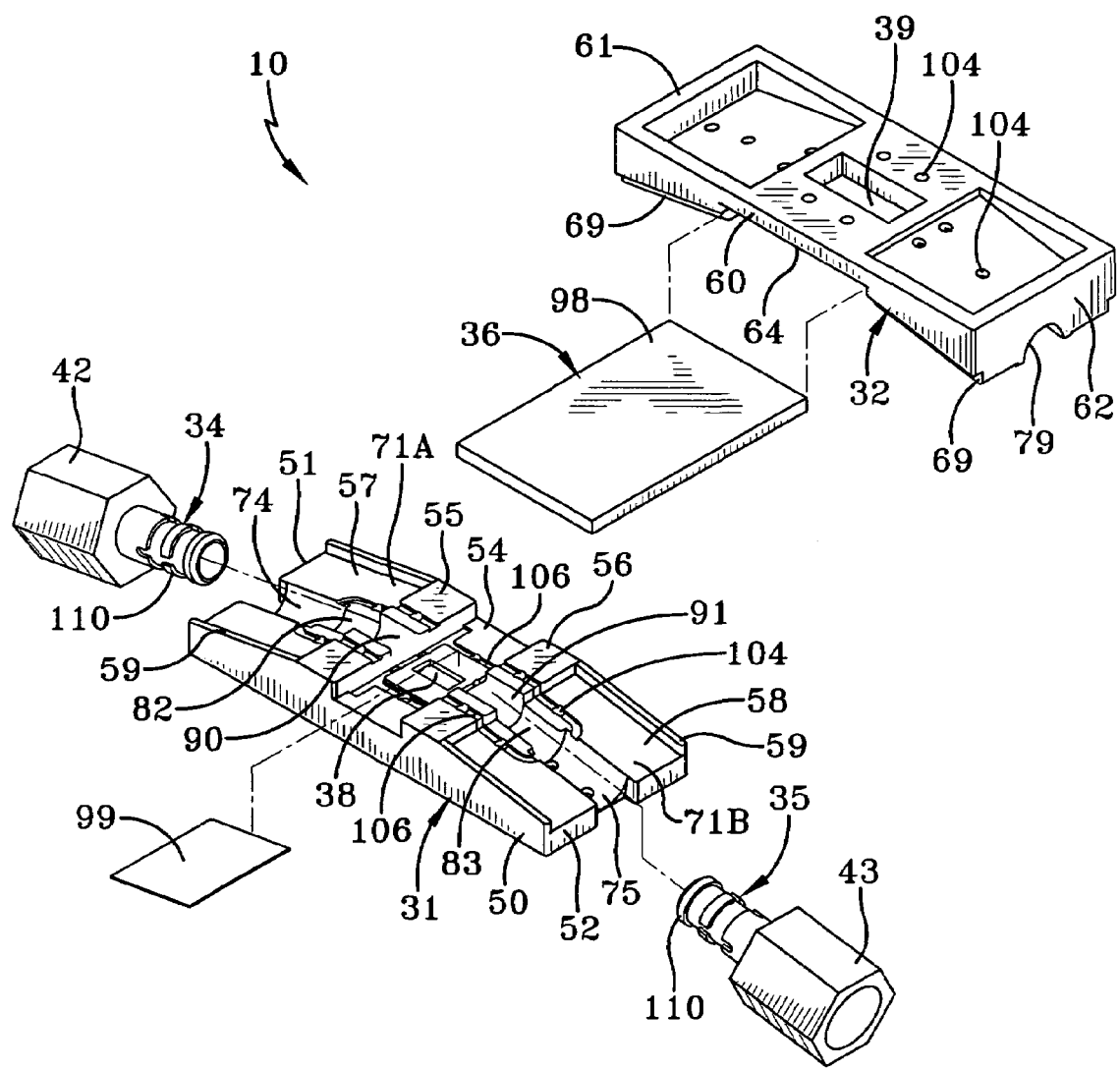
FIG. 1C is an exploded view of the optical flow cell showing a first and a second portion of a two-piece shell of the optical flow cell.

Referring now to FIGS. 1A, 1B, and 1C, it can be seen that the optical flow cell 10 according to the present invention includes a two-piece shell 30. The two-piece shell 30 includes a first portion 31 and a second portion 32. When assembled, the first portion 31 and the second portion 32 support an inlet tube 34, an outlet tube 35, and a viewing assembly 36.

To facilitate transmission of light into the fluid sample material, the first portion 31 provides a light entry aperture 38, and the second portion provides an imaging aperture 39. When the optical flow cell is positioned in the fluid sample inspection system 12, the light entry aperture 38 is positioned proximate the light source 24, and the imaging aperture 39 is positioned adjacent the imaging system 26. As such, the light entry aperture 38 and imaging aperture 39 allow light transmission through, and visual access to the viewing assembly 36 and the sample material moving through the optical flow cell 10.

The inlet tube 34, the outlet tube 35, and the viewing assembly 36 are ultimately retained between the first portion 31 and the second portion 32. The inlet tube 34 and the outlet tube 35 are respectively provided with an inlet fitting 42 and an outlet fitting 43. The inlet fitting 42 and the outlet fitting 43 are both threaded and allow the conduits (not shown) from the input container 14 and output container 18 to be respectively attached thereto.

As discussed above, the sample fluid material initially contained in the container 14 is transferred by the operation of pressure source 13 and pump 16 through the optical flow cell 10. Aiding the passage (or flow) of the sample fluid material through the optical flow cell 10 is the configuration of the first portion 31 and second portion 32. For example, the first portion 31 and second portion 32 include sections which are canted to impact the orientation of the inlet tube 34 and outlet tube 35 when contained therein. Moreover, these sections transition the sample fluid material between the circular cross-sectioned inlet tube 34 and viewing assembly 36, and between viewing assembly 36 and the circular cross-sectional outlet tube 35.

Figure 2A:
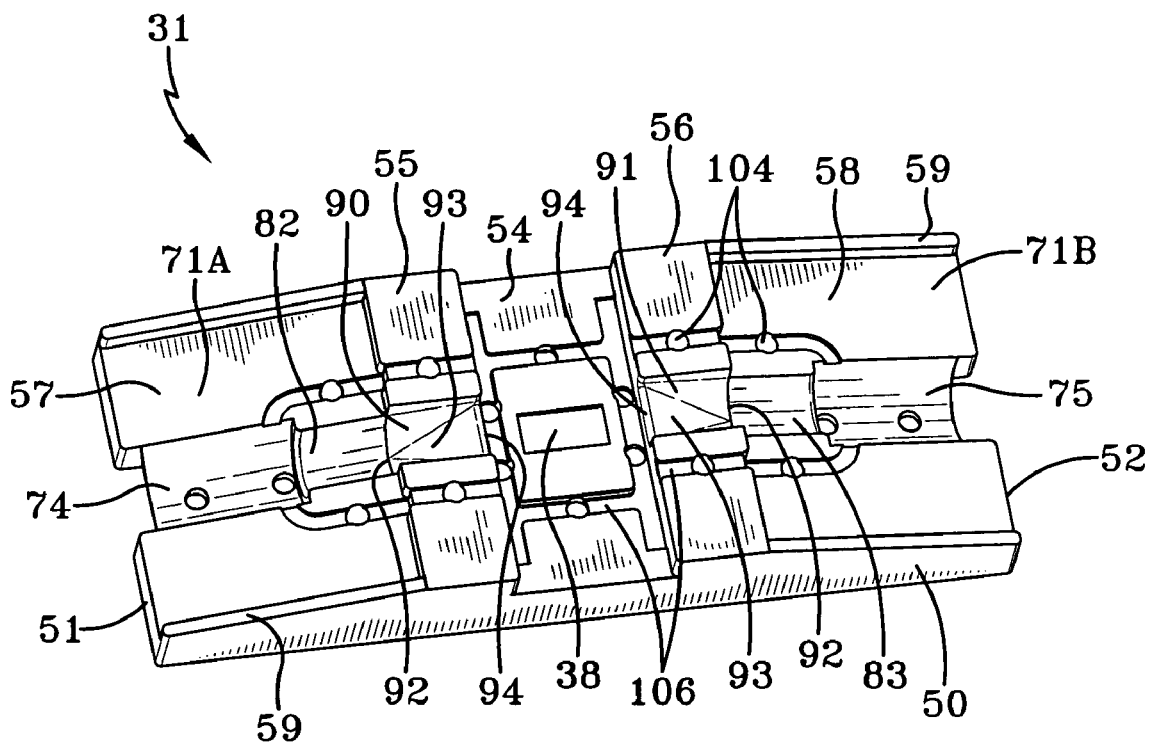
FIG. 2A is a top perspective view of the first portion.
Figure 2B:
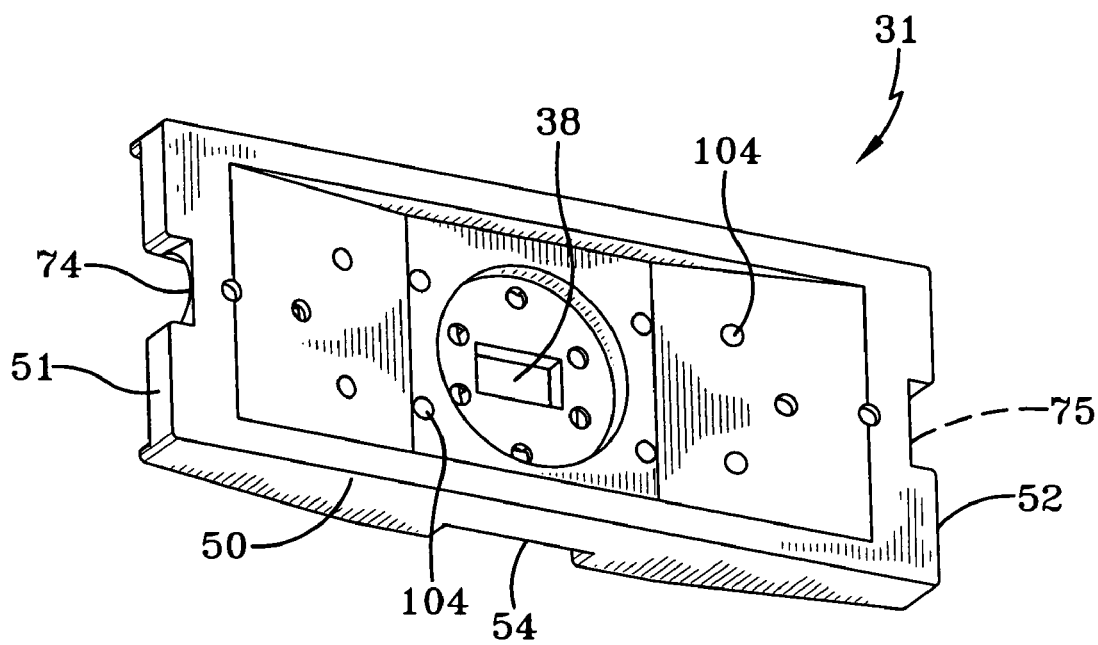
FIG. 2B is a bottom perspective view of the first portion.
Figure 3A:
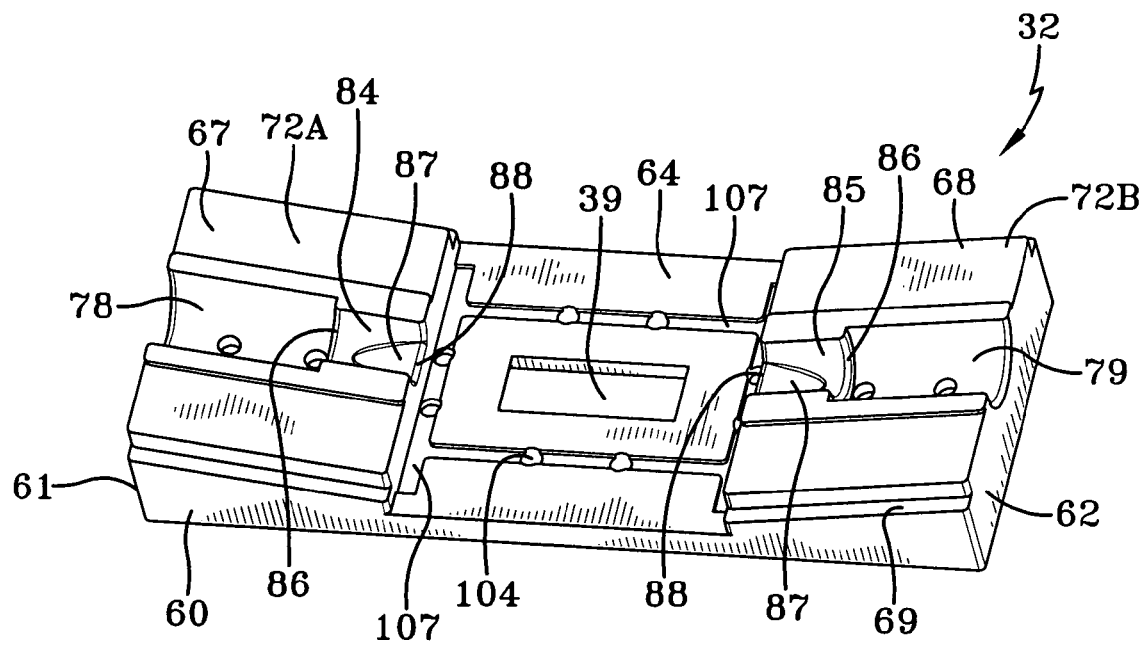
FIG. 3A is a top perspective view of the second portion.
Figure 3B:
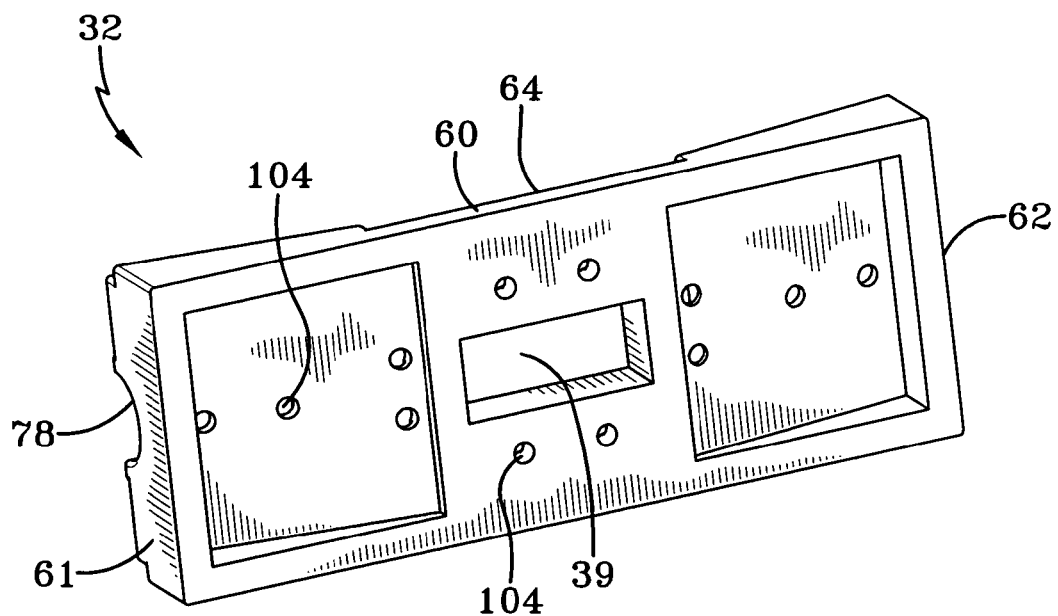
FIG. 3B is a bottom perspective view of the second portion.

As seen in FIGS. 2A and 3A, the first portion 31 and the second portion 32 are configured to mate with and accept one another, as well as the inlet tube 34, the outlet tube 35, and the viewing assembly 36. The first portion 31 and second portion 32 are manufactured of polymer materials ideally through an injection molding process. Therefore, the manufacture of the first portion 31 and second portion 32 can be relatively inexpensive, and can accomplished to close tolerances.

The first portion 31 includes a base 50 extending between an inlet end 51 and an outlet end 52. A first channel 54 is defined between segments 55 and 56 which extend upwardly from the base 50. Also extending upwardly from the base 50 are sloped segments 57 and 58, and rail sets 59. The rail sets 59 partially define the boundaries of the sloped segments 57 and 58, and as discussed below, aid in the engagement of the first portion 31 and second portion 32.

Like the first portion 31, the second portion 32 includes a base 60 extending from an inlet end 61 to an outlet end 62. Furthermore, a second channel 64 is defined between sloped segments 67 and 68 which extend upwardly from the base 60. Partially defining the boundaries of the sloped segments 67 and 68 are ridge sets 69. Like the rail sets 59 provided on the first portion 31, the ridge sets 69 aid in the engagement of the first portion 31 and second portion 32.

When the first portion 31 and the second portion 32 are interfaced with one another the close tolerances provide for a "snug" fit, where the sloped segments 57, 58 are positioned adjacent to and engage the sloped segments 67, 68, respectively. Furthermore, the first channel 54 cooperates with the second channel 64 to define a space for receiving and accommodating the viewing assembly 36. To that end, the surfaces 71A and 71B extending across the sloped segments 57 and 58, respectively, form supplementary angles in relation to the surfaces 72A and 72B extending across the sloped segments 67, 68, respectively. That is, the angle of the surface 71A is supplementary with respect to the angle of the surface 72A, and the angle of the surface 71B is supplementary with respect to the angle of the surface 72B. As such, the orientation of the sloped surfaces 71A, 71B and sloped surfaces 72A, 72B allow the first portion 31 and second portion to interface without significant gaps between these surfaces, although gaps may be permitted depending upon the sizing of the rails sets 59 and ridge sets 69.

When the first portion 31 and second portion 32 are engaged, the rail sets 59 provided along the sloped segments 57, 58, and the ridge sets 69 provided along the sloped segments 67, 68 further enhance the interface of the first portion 31 and second portion 32. For example, when the two-piece housing 30 is assembled, the rail sets 59 are received in the ridge sets 69, thereby properly locating the first portion 31 with respect to the second portion 32.

As discussed above, the angles of the sloped segments 57, 58 and sloped segments 67, 68 angularly orient the inlet tube 34 and outlet tube 35 with respect to the first portion 31 and second portion 32. For example, as seen in FIGS. 2A and 3A, the first portion 31 and the second portion 32 each have receiving notches for orienting the inlet tube 34 and the outlet tube 35. The first portion 31 includes an inlet tube receiving notch 74 and an outlet tube receiving notch 75 formed within the sloped segments 57, 58, respectively.

Furthermore, the second portion includes an inlet tube receiving notch 78 and an outlet tube receiving notch 79 formed within the sloped segments 67 and 68, respectively.

Ultimately, when the housing two-piece shell 30 is assembled the inlet tube receiving notch 74 opposes the inlet tube receiving notch 78, and the outlet tube receiving notch 75 opposes the outlet tube receiving notch 79. Therefore, when the inlet tube 34 and outlet tube 35 are retained between the first portion 31 and second portion 32, the inlet tube 34 is positioned between the inlet tube receiving notches 74 and 78, and the outlet tube 35 is captured between the outlet tube receiving notches 75 and 79.

Provided adjacent the inlet tube receiving notch 74 and the outlet tube receiving notch 75, and formed within the sloped segment 57, 58 are semi-cylindrical transition notches 82 and 83. The semi-cylindrical transition notches 84 and 85 are oppositely oriented on either side of the first channel 54. Furthermore, provided adjacent the inlet tube receiving notch 78 and the outlet tube receiving notch 79, and formed within the sloped segments 67, 68 are first specially-configured transition notches 84 and 85 that are oppositely oriented on either side of the second channel 64. The first specially-configured transition notches 78 and 79 include first end portions 86, tapered portions 87, and second end portions 88. Because the first specially-configured transition notches 78 and 79 are oppositely oriented on either side of the second channel 64, the tapered portions 87 thereof canted oppositely.

When the two-piece housing 30 is assembled, the semi-cylindrical notches 82 and 83 oppose the first specially-configured transition notches 84 and 85. Like the semi-cylindrical transition notches 82 and 83, the first end portions 86 have radii matching the radii of the inlet tube 34 and outlet tube 35.

Provided adjacent the semi-cylindrical transition notches 82 and 83, and formed within the segments 55, 56 are second specially-configured transition notches 90 and 91. When the two-piece housing 30 is assembled, the second specially-configured transition notches 90 and 91 are opposed to a portion of the viewing assembly 36 (a reference plate 98) because of the comparatively large width of the first channel 54 as compared to the second channel 64. Like the first specially-configured transition notches 84 and 85, the second specially-configured transition notches 90, 91 also have a first end portion 92, a tapered portion 93, and a second end portion 94.

Figure 4:
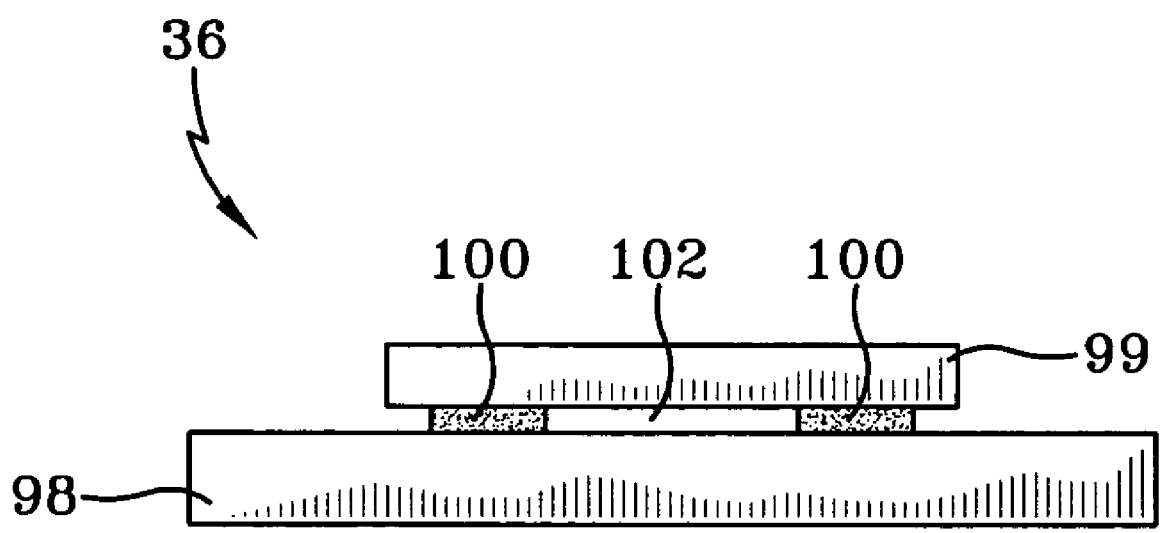
FIG. 4 is a cross sectional view of a viewing assembly during manufacture thereof.

The construction of the viewing assembly 36 is best seen in FIG. 4, and includes the reference plate 98 and a sealing plate 99. The plates 98 and 99 are typically glass plates with excellent optical properties. The reference plate 98 is the longer of the two plates, and extends beyond the edges of the two-piece housing 30 (as seen in FIGS. 1A and 1B). Furthermore, the reference plate 98 has a closely controlled thickness, which provides a mechanical datum for a repeatable focus position for the imaging system 26.

As seen in FIG. 4, the reference plate 98 is adapted to accept two spaced apart substantially parallel bonding strips 100. In addition to adhering the reference plate 98 and the sealing plate 99 together, the bonding strips serve to separate the plates from one another to define a flow channel 102 therebetween.

The flow channel 102 has a rectangular cross section, and the above-described configuration of the first portion 31 and second portion 32 between the inlet tube 34 and the viewing assembly 36 and between the outlet tube 35 and the viewing assembly 36 provides a smooth and uniform transition between the circular cross-section inlet tube 34 and outlet tube 35, and the rectangular cross-sectioned flow channel 102.

Before the inlet tube 34, the outlet tube 35, and the viewing assembly 36 are inserted between the first portion 31 and a second portion 32, the interior surfaces of the first and second portions 31 and 32 are exposed to a corona treatment. The material utilized in manufacturing the first portion 31 and a second portion 32 was selected to be highly resistant to the chemical environment it will operate in, and the corona treatment serves to increase the surface energy thereof prior to bonding.

To further enhance the bonding of the first portion 31 and the second portion 32 together, both portions are provided with various apertures 104. Therefore, during the bonding process, a bonding material (i.e. epoxy resin) is injected into the various apertures 104 to ultimately flow between the first and second portions 31 and 32 to join the two-piece shell 30 together.

In addition, bonding channels 106, 107 are provided on the interior surfaces of the first portion 31 and a second portion 32, respectively. For example, on the first portion 31, the bonding channels 106 are cut into the segments 55, 56, sloped segments 57, 58, and first channel 54, and on the second portion 32, the bonding channels 107 are cut into the second channel 64. The channels 106, 107 direct the flow of epoxy resin between the first portion 31 and second portion 32 during injection, and therefore, provide good adhesion between all of the required surfaces. Additionally, the inlet tube 34 and the outlet tube 35 include ribs 110 which enhance the rotational mechanical stability of the inlet tube 34 and the outlet tube 35 in the two piece shell 30, and enhance the leak prevention in the optical flow cell 10.

When the optical flow cell 10 is assembled, the transition provided between the inlet tube 34 and the flow channel 102, and between the outlet tube 35 and the flow channel 102 allows the sample fluid material to efficiently transition between the circular cross-sectioned inlet tube 34 and the rectangular cross-sectioned flow channel 102 and between the rectangular cross-section flow channel 102 and the circular cross-sectioned outlet tube 35.

For example, the sample fluid material exiting the inlet tube 34 enters the area defined by the semi-cylindrical transition notch 82 and the first specially-configured transition notch 84. The tapered portion 87 (between the first end portion 86 and the second end portion 88) serves to flatten the flow pattern of the fluid sample material. Thereafter, the sample fluid material enters the area defined by the second specially-configured transition notch 90 and the reference plate 98. The tapered portion 93 (between the first end portion 92 and the second end portion 94) also serves to flatten the flow pattern of the fluid sample material. The flattening of the flow pattern of the sample fluid material effectively transitions the flow from the inlet tube 34 to the flow channel 102. As such, the configuration of the first portion 31 and second portion 32 prepares the sample fluid material to smoothly flow from the circular cross-sectioned inlet tube 34 to the rectangular cross-sectioned flow channel 102.

During travel through the flow channel 102, the fluid sample material can be analyzed by the fluid sample inspection system 12. After being analyzed by the fluid sample inspection system 12, the sample fluid material exits the flow channel 102. Upon exiting the flow channel 102, the sample fluid material enters the area defined by the second specially-configured transition notch 91 and the reference plate 98. The tapered portion 93 of the second specially-configured transition notch 91 and the tapered portion 93 of the second specially-configured transition notch 90 are canted oppositely. As such, rather than serving to flatten the flow of the sample fluid material, the tapered portion 93 of the second specially-configured transition 91 allows flow of the sample fluid material to expand.

Thereafter, the flow of the sample fluid material enters the area defined by the semi-cylindrical transition notch 83 and first specially-configured transition notch 85. Again, like tapered portions 93, the tapered portions 97 of the first specially-configured transition notch 85 and of the first specially-configured transition notch 84 are canted oppositely. As such, rather than serving to flatten flow of the sample fluid material, the tapered portion of the first specially-configured transition notch 85 allows the flow of the sample fluid material to expand. The transitioning provided by the first portion 31 and second portion 32 downstream of the flow channel 102 allows the flow pattern of the sample fluid material (flattened by its transition into and through the flow channel 102) to be modified before entering the outlet tube 35. As such, the configuration of the first portion 31 and second portion 32 prepares the sample fluid material to smoothly flow from the rectangular cross-sectioned flow channel 102 to the circular cross-sectioned outlet tube 35.

Consequently, the optical flow cell 10 has many advantages over the prior art. By employing a reference plate 98 that extends beyond the edges of the two-piece housing 30, the reference plate 98 is easily used as a repeatable reference point to place the optical flow cell 10 in a predetermined location in the imaging system 26. As those skilled in the art will appreciate, proper positioning of the optical flow cell 10 (and the viewing assembly 36) in the imaging system 26 is of critical importance because of the typical small size of the particulate matter being monitored. Moreover, because the optical flow cell 10 is manufactured within small tolerances, the reference point provided by the reference plate 98 is repeatable between alternative examples of the optical flow cell 10 installed in the imaging system 26. Furthermore, the configuration of the first portion 31 and second portion 32 provide a smooth flow pattern for the sample fluid material through the optical flow cell. Such transitioning of the sample fluid material decreases turbulence, and allows the particles suspended in the sample fluid material to be analyzed by the fluid sample inspection system 12. Moreover, the use of first portion 31 and second portion 32 are relatively inexpensive to manufacture, and because of their configurations, provide for faster assembly of the optical flow cell 10. In fact, the first portion 31 and second portion 32 serve to eliminate the time-consuming potting process associated with the prior art, and simultaneously increase the tolerances under which the optical flow cell 10 is manufactured. As such, the close tolerances associated with the optical flow cell 10 provide for repeatable reference points. That is, the close tolerances insure substantially similar dimensions between manufactured optical flow cells 10, thereby substantially eliminating time consuming adjustments to the fluid sample inspection system 12 to accommodate dimensional differences associated with prior art optical flow cells.

Thus, it should be evident that the optical flow cell 10 disclosed herein carries out one or more of the objects of the present invention set forth above and otherwise constitutes an advantageous contribution to the art. As will be apparent to persons skilled in the art, modifications can be made to the preferred embodiment disclosed herein without departing from the spirit of the invention, the scope of the invention herein being limited solely by the scope of the attached claims.

The invention claimed is:

1. An optical flow cell, comprising:
a two-piece shell formed from separate first and second portions, said portions each having an inner surface providing a bonding channel adapted to receive a bonding material for joining said first and second portions together, wherein said first portion provides a light entry aperture, and said second portion provides an imaging aperture;
an inlet tube and an outlet tube retained between said first portion and said second portion; and
a viewing assembly retained between said first portion and said second portion, wherein said viewing assembly includes a reference plate and a flow channel, said flow channel fluidly communicating with said inlet tube and said outlet tube.

2. An optical flow cell according to claim 1, wherein said reference plate extends from said shell, and serves as a repeatable reference point to properly position the optical flow cell.

3. An optical flow cell according to claim 1, wherein said reference plate is separated from a sealing plate by bonding strips, said flow channel being formed between said bonding strips.

4. An optical flow cell according to claim 1, wherein said first portion and said second portion each include viewing assembly channels adapted to accommodate said viewing assembly, when said viewing assembly is retained between said first portion and said second portion.

5. An optical flow cell according to claim 1, wherein said first portion includes an inlet tube receiving notch and an outlet tube receiving notch and said second portion includes an inlet tube receiving notch and an outlet tube receiving notch, and when said inlet tube and said outlet tube are retained within said shell, said inlet tube is positioned between said inlet tube receiving notches and said outlet tube is positioned between said outlet tube receiving notches.

6. An optical flow cell according to claim 1, wherein said inlet tube has a circular cross section, said outlet tube has a circular cross section, and said flow channel has a rectangular cross section, said first portion and said second portion configured to smoothly transition flow of a sample fluid material between said first outlet tube and said flow channel and between said flow channel and said second outlet tube.

7. An optical flow cell according to claim 6, further comprising a first channel provided on said first portion, and semi-cylindrical transition notches oppositely oriented on either side of said channel, a second channel provided on said second portion, and first specially-configured transition notches are oppositely oriented on either side of said second channel, said specially-configured transition notches each including a tapered portion, and said semi-cylindrical transition notches and said first specially-configured transition notches opposed to one another on either side of said channel when said optical flow cell is assembled.

8. An optical flow cell according to claim 7, wherein second specially-configured transition notches are provided adjacent said second semi-cylindrical transition notches on said first portion, said second specially-configured transition notches opposing a plate of said viewing assembly when said optical flow cell is assembled.

9. An optical flow cell according to claim 1, wherein at least one of said first and second portions have at least one flow aperture adapted to receive the bonding material which is directed into one of said bonding channels.

10. An optical flow cell, comprising:
a first portion, wherein said first portion provides a light entry aperture;
a second portion, wherein said second portion provides an imaging aperture;
an inlet tube and an outlet tube retained between said first portion and said second portion; and
a viewing assembly retained between said first portion and said second portion, said viewing assembly including a reference plate and a flow channel, said flow channel fluidly communicating with said inlet tube and said outlet tube, wherein said inlet tube has a circular cross section, said outlet tube as a circular cross section, and said flow channel has a rectangular cross section, said first portion and said second portion configured to smoothly transition flow of a sample fluid material between said first outlet tube and said flow channel and between said flow channel and said second outlet tubes, said first portion and said second portion mate with one another to capture said inlet tube, said outlet tube and said viewing assembly therebetween.

11. The optical flow cell according to claim 10, wherein said first portion includes at least one rail set.

12. The optical flow cell according to claim 11, wherein said second portion includes at least one ridge set, said ridge set configured to receive said at least one rail set of said first portion.

13. The optical flow cell according to claim 12, wherein at least one of said first portion and said second portion contains at least one aperture configured to receive bonding material.

14. The optical flow cell according to claim 13, wherein said portion containing said at least one aperture includes at least one bonding channel adapted to receive bonding material therefrom.

* * * * *